| United States Patent [19] | [11] Patent Number: 4,549,009 |
| Higaki et al. | [45] Date of Patent: Oct. 22, 1985 |

[54] POLYMERIC GLYCOL ESTER

[75] Inventors: Yuzo Higaki, Tokyo; Akitoshi Ukai, Yokohama, both of Japan

[73] Assignee: The Nisshin Oil Mills, Ltd., Tokyo, Japan

[21] Appl. No.: 612,750

[22] Filed: May 21, 1984

Related U.S. Application Data

[63] Continuation of Ser. No. 57,507, Jul. 13, 1979, , which is a continuation of Ser. No. 821,306, Aug. 2, 1977, abandoned.

[30] Foreign Application Priority Data

Aug. 10, 1976 [JP] Japan .................................. 51-94454

[51] Int. Cl.$^4$ ............................................. C08G 63/66
[52] U.S. Cl. .................................... 528/301; 528/272
[58] Field of Search ................................ 528/272, 301

[56] References Cited

U.S. PATENT DOCUMENTS 3,330,731 7/1967 Mehaffey ...................... 424/DIG. 2
3,864,315 2/1975 Ohno et al. ...................... 528/301 X
3,993,629 11/1976 Hasunuma et al. ................. 528/301

FOREIGN PATENT DOCUMENTS 50-132134 10/1975 Japan .

*Primary Examiner*—Lucille M. Phynes
*Attorney, Agent, or Firm*—Bacon & Thomas

[57] ABSTRACT

A cosmetic containing a polymeric ester or a salt or amide thereof as a base, the polymeric ester being obtained by reacting a certain polymeric glycol having both ethylene glycol units and propylene glycol units in the molecule with a saturated aliphatic dicarboxylic acid and/or hydroxydicarboxylic acid.

7 Claims, No Drawings

POLYMERIC GLYCOL ESTER

This application is a continuation, of application Ser. No. 057,507, filed July 13, 1979 pending, which is a continuation of Ser. No. 821,306, filed Aug. 2, 1977 abandoned.

This invention relates to cosmetics and, more particularly, to a cosmetic for the hair or skin in which a polymeric ester, obtained by reacting a certain polymeric glycol with a dicarboxylic acid, or a salt or amide thereof is contained as a base.

Prior art oil-based hairdressings such as hair oil and pomade have animal or vegetable fats and oils, mineral oils, and the like for their principal ingredients. Though excellent in hairdressing effect, they make the hair oily, fail to achieve a hairdo softly, and do not permit the hair to be shampooed easily. Moreover, the hands stained with them cannot be easily cleaned by washing with water alone.

In order to overcome the disadvantages of these oil-based hairdressings, various attempts have been made with no satisfactory result.

For example, the addition of various nonionic surface active agents allow the fat and oil ingredients to be suspended and dispersed in water. However, the resulting products lose their hairdressing effect and dissolve combs and spectacle frames made of celluloid.

Cosmetics based on polyalkylene glycols such as polyethylene glycol and polypropylene glycol are also known. However, polyethylene glycol attacks celluloid and becomes solid when its molecular weight exceeds 1,500. On the other hand, polypropylene glycol remains liquid even at higher molecular weights, but shows a reduction in hydrophilic nature and viscosity and a lack of hairdressing effect.

Furthermore, polymeric glycols of the type derived from the block polymerization of polyethylene glycol and polypropylene glycol are known as compounds having an improved hydrophilic nature and a reduced attacking action on celluloid. However, their viscosity is insufficient to make them useful as a base for hairdressings.

There is a well-known method of raising viscosity by adding polypropylene glycol to lower alcohols or polyhydric alcohols. However, the resulting product does not serve as a base having a satisfactory hairdressing effect. The phosphate-crosslinked esterification products of alkylene glycols are also known as compounds having a considerable degree of viscosity. However, they involve great difficulties in controlling their viscosity and have the undesirable property of irritating the eyelids.

In Japanese Patent Application Disclosure No. 132139/75 (laid open to the public inspection on Oct. 20, 1975), cosmetics are described which contain an esterification product obtained by reacting propylene glycol, dipropylene glycol and/or polypropylene glycol with a saturated aliphatic dicarboxylic acid and/or saturated aliphatic hydroxydicarboxylic acid. In this esterification product, considerable improvements have been made on its attacking action on celluloid, hairdressing effect (viscosity), and hydrophilic nature. In preparing this compound, however, severe conditions for esterification reaction are required because of the high percentage of secondary hydroxyl groups in the propylene glycol serving as the backbone. Consequently, the resulting esterification product is not completely satisfactory with regard to its color and odor.

It is an object of this invention to provide a novel cosmetic which overcomes the above-described disadvantages.

It is another object of this invention to provide a cosmetic which is hydrophilic, has an excellent hairdressing effect, permits any hairdo to be achieved softly, exerts no attacking action on celluloid, and develops little color or odor.

It is still another object of this invention to provide a cosmetic for hair and skin treatment.

In accordance with this invention, there is provided a cosmetic containing a polymeric ester or a salt or amide thereof as a base, said polymeric ester being obtained by reacting (A) at least one polymeric glycol represented by the general formula

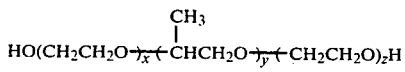

where the sum of x and z has an average value of from 1 to 50, y has an average value of from 10 to 60, and the total content of ethylene glycol units in all molecules is from 5 to 50% by weight, with (B) at least one carboxylic acid selected from the group consisting of saturated aliphatic dicarboxylic acids and saturated aliphatic hydroxydicarboxylic acids.

A part of the reactant A may be replaced by propylene glycol, dipropylene glycol, and/or polypropylene glycol.

The aforesaid polymeric ester also falls within the scope of this invention.

The reactant A which is one of the reactants to be used for preparing the polymeric ester of the invention comprises, as described hereinabove, at least one polymeric glycol of the type derived from the block polymerization of polyethylene glycol and polypropylene glycol, represented by the general formula

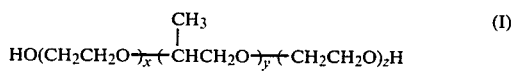

In the above formula (I), the sum of x and z has an average value of from 1 to 50, preferably from 3 to 20, and y has an average value of from 10 to 60 (corresponding to the molecular weight of polypropylene glycol ranging from about 600 to about 3,500), preferably from 15 to 40. The content of ethylene glycol units (or polyethylene glycol) in the above formula (I) is from 5 to 50% by weight, preferably from 10 to 50% by weight, and more preferably from 10 to 30% by weight.

The process for preparing the above-described polymeric glycol will be apparent to those skilled in the art. Generally, propylene glycol and propylene oxide are addition-reacted in the presence of an alkaline catalyst such as sodium hydroxide or pottasium hydroxide to yield crude polypropylene glycol having a desired molecular weight. After neutralization and purification by filtration, the above crude polypropylene glycol and ethylene oxide are addition-reacted under similar conditions to yield the desired polymeric glycol.

Many examples of the above-described polymeric glycol are commercially available. They include, for instance, Epan 410, 420, 450, 720 and 740 manufactured and sold by the Daiichi Kogyo Seiyaku co., Ltd. as well as Pluronic L-31, L-44, L-61, L-62 and L-64 manufactured and sold by the Asahi Denka Co., Ltd.

The reactant B which is reacted with the reactant A to produce the polymeric ester of the invention comprises at least one carboxylic acid selected from the group consisting of saturated aliphatic dicarboxylic acids and saturated aliphatic hydroxydicarboxylic acids. The saturated aliphatic dicarboxylic acids can be represented by the general formula

$$\text{HOOC-R-COOH} \tag{II}$$

where R is a saturated aliphatic group. Practically, R is an alkylene group having from 2 to 8 carbon atoms. Preferred examples of these dicarboxylic acids include malonic acid, succinic acid, glutaric acid, adipic acid, pimelic acid, suberic acid, azelaic acid, sebacic acid, and the like. Among others, succinic acid is the most preferred.

The saturated aliphatic hydroxydicarboxylic acids are such compounds as can be represented by the above formula (II) in which the R group has one or more hydroxyl substituents. Preferred examples include malic acid and tartaric acid.

The esterification reaction between the reactants A and B may be performed according to any of the conventional procedures. Usually, the reactants A and B are mixed in a molar ratio of from 1.5:1 to 1:1.5 and heated in the presence or absence of a catalyst to yield the desired polymeric ester. This esterification reaction is generally carried out at a temperature of from 160° C. to 250° C., preferably from 190° C. to 230° C. for a period of from 5 to 30 hours in the presence of an inert refluxing solvent such as toluene or xylene. If the use of a catalyst is desired, conventional esterification catalysts such as sulfuric acid, hydrochloric acid, toluenesulfonic acid, boron trifluoride, and the like may be employed.

In carrying out the esterification reaction, a part, usually from 10 to 80% by weight and especially from 10 to 50% by weight, of the reactant A (polymeric glycol) may be replaced, as described hereinabove, by propylene glycol, dipropylene glycol, and/or polypropylene glycol having a molecular weight of from 400 to 1,500. In this case, the conditions for esterification reaction (such as reaction temperature, reaction time, and the like) need be made somewhat severer. However, the resulting ester has a hydrophilic nature and exerts no attacking action on celluloid, thus presenting no problem from a practical point of view.

As described hereinabove, the esterification reaction proceeds under relatively mild conditions, so that little color or odor is developed and a product having any desired viscosity can be obtained.

Generally, the polymeric ester of the invention is what is called on oligomeric esterification product having an average molecular weight of from 2,500 to 50,000, in which the properties of a monomer are present in combination of those of a polymer. In addition, its viscosity, melting point, molecular weight, hydrophilic nature, and other parameters can be arbitrarily changed over a wide range, whereby correspondingly characteristic cosmetics can be prepared. Incidentally the polymeric ester of the invention generally has a viscosity ranging between 500 centipoises and that of a paste.

If an excess of the acid is used in the esterification reaction, a product having an acid value is yielded. These acid moieties may be partially or totally reacted with alkali metals, such as sodium, potassium, and the like, or amines, such as ethanolamine, diethanolamine, triethanolamine, triethylamine, morpholine, and the like, to form metal salts or amine salts. Alternatively, they may also be amidized.

The polymeric ester of the invention or a salt or amide thereof is not only characterized by the properties of having a hydrophilic nature and exerting no attacking action on celluloid, but also by the property of being viscous. Accordingly, it is useful as a base for hairdressings, so that hairdressings containing it have an excellent hairdressing effect, make the hair flexible rather than sticky, and permit any hairdo to be achieved softly. Moreover, the hands stained therewith can be easily cleaned by washing with water alone and the hair can be shampooed easily.

Since the polymeric ester of the invention or a salt or amide thereof is an esterification product derived from a polymeric glycol (which is an etherification product) and a dicarboxylic acid, ether linkages and ester linkages, and occasionally terminal hydroxyl groups, are incorporated in the molecule. This causes intermolecular association to take place, whereby a higher viscosity is advantageously achieved even at the same molecular weight as that of the oil ingredient of a prior art hairdressing. Furthermore, since its hydrophilic nature and viscosity create a gelling action, dispersing action, solubilizing action, moisture-retaining action, and the like, the polymeric ester of the invention or a salt or amide thereof may also be applied to cosmetics for the skin, such as cream, lotion, and the like.

In order to prepare a cosmetic in accordance with this invention, the conventional base, gelling agent, and the like are partially or totally replaced by the polymeric ester of the invention or a salt or amide thereof.

A cosmetic for hair treatment according to this invention includes a liquid type and a paste type such as pomade and stick pomade. A liquid hair cosmetic can be readily prepared by dissolving the polymeric ester of the invention or a salt or amide thereof in a solvent, such as water containing ethanol, polypropylene glycol, or the like, which is commonly used in prior art hairdressings. Generally, this hairdressing contains the polymeric ester of the invention or a salt or amide thereof at a concentration of from 5 to 50% and preferably from 10 to 30%. If desired, a perfume and/or antioxidant may be added thereto. A paste hair cosmetic usually contains 5 to 100%, preferably 5 to 80% by weight of the polymeric ester or salts or amides thereof. If desired, glycols, waxes, perfumes and/or antioxidants may be added thereto.

A cosmetic for the skin can also be prepared by dissolving the compound of the invention in a solvent such as ethanol, glycerol, water, or the like. Generally, this cosmetic for the skin contains the compound of the invention at a concentration of from 1 to 50% and preferably from 1 to 20%. A perfume and/or alum may be suitably added thereto.

This invention will be more fully understood from the following examples. All part and percentages are by weight unless otherwise indicated.

EXAMPLES 1-16

Into a one-liter four neck flask equipped with stirrer, thermometer, nitrogen gas inlet tube and water separator, polymeric glycol and dicarboxylic acid ingredients as listed in Table 1 were charged in the indicated proportion. Based on the total weight of this mixture, 5% of xylene and 0.3% of p-toluenesulfonic acid were added. The resulting reaction mixture was heated at 160°–250° C. with stirring while nitrogen gas was being blown therethrough. After completion of the reaction, xylene was added. The reaction product was washed with water, vacuum-dried, and deodorized with steam at reduced pressure to yield esters having properties as listed in Table 2. For purposes of comparison, the properties of some polymeric glycols themselves are also given.

In order to examine the presence of primary irritating properties to the human body, a closed patch test was performed as follows: After removing the horny layer and sebum from a skin area located on the flexion side of the forearm or upper arm, a 1×1 inch piece of lint cloth having a sample spread thereon was applied to that skin area, overlaid by oilpaper, fastened with adhesive tape applied in parallel crosses, and then covered with a bandage. This test was carried out on 20 healthy subjects and examination was made after 24 hours, 48 hours and 1 week. In addition, the development of odor after application was tested as follows: About 0.2 g of sample was applied to a 2×2 inch area of the forearm and examined, by smelling, for odor after 10, 20 and 30 minutes as well as after 1, 4 and 8 hours. This test was carried out on 20 healthy subjects. The results of these tests are also given in Table 2.

TABLE 1

| | | Reactant A | | | | | |
|---|---|---|---|---|---|---|---|
| | | Polymeric Glycol (1) | | | Average Molecular | | |
| Example | Reactant B | Compound | x + z* | y* | Polyethylene Glycol Content (%) | Weight of Polypropylene Glycol (2) | Weight Ratio (1)/(2) | Molar Ratio A/B |
| Control 1 | — | Epan 420** | 6.4 | 20.6 | 20 | — | — | — |
| Control 2 | — | Epan 740** | 29.9 | 34.4 | 40 | — | — | — |
| 1 | Succinic acid | Epan 405** | 1.0 | 20.6 | 5 | — | — | 1.1/1.0 |
| 2 | " | Epan 410** | 2.6 | 20.6 | 10 | — | — | 1.15/1.0 |
| 3 | " | Epan 420 | 6.4 | 20.6 | 20 | — | — | 1.2/1.0 |
| 4 | " | Epan 450** | 27.2 | 20.6 | 50 | — | — | 1.25/1.0 |
| 5 | " | Epan 720** | 11.4 | 34.4 | 20 | — | — | 1.2/1.0 |
| 6 | " | Epan 740 | 29.9 | 34.4 | 40 | — | — | 1.25/1.0 |
| 7 | Adipic acid | Epan 720 | 11.4 | 34.4 | 20 | — | — | 1.2/1.0 |
| 8 | Azelaic acid | Epan 720 | 11.4 | 34.4 | 20 | — | — | 1.2/1.0 |
| 9 | Succinic acid | Pluronic L-62*** | 9.5 | 30.0 | 20 | — | — | 1.15/1.0 |
| 10 | Malic acid | Epan 720 | 11.4 | 34.4 | 20 | — | — | 1.2/1.0 |
| 11 | Succinic acid | Epan 420 | 6.4 | 20.6 | 20 | ca.1000 | 3/7 | 1.2/1.0 |
| 12 | " | Epan 420 | 6.4 | 20.6 | 20 | " | 7/3 | 1.2/1.0 |
| 13 | " | Epan 450 | 27.2 | 20.6 | 50 | " | 3/7 | 1.3/1.0 |
| 14 | " | Epan 720 | 11.4 | 34.4 | 20 | " | 5/5 | 1.2/1.0 |
| 15 | " | Epan 420 | 6.4 | 20.6 | 20 | ca.1500 | 5/5 | 1.2/1.0 |
| 16 | Malic acid | Epan 420 | 6.4 | 20.6 | 20 | ca.1000 | 3/7 | 1.2/1.0 |

*x, y and z are as previously defined for the formula (1).
**These are the trade names of products manufactured and sold by the Daiichi Kogyo Seiyaku Co., Ltd.
***This is the trade name of a product manufactured and sold by the Asahi Denka Co., Ltd.

TABLE 2

| | Properties of Ester | | | | | | |
|---|---|---|---|---|---|---|---|
| Example | Acid Value | Solubility in 50% Ethanol/Water* | Viscosity at 25° C. (poises) | Attack on Celluloid** | Color | Irritation | Odor |
| Control 1 | — | 100 or more | 2.1 | No | none-slightly pale yellow | No | Yes |
| Control 2 | — | 100 or more | Pasty | Yes | none-slightly pale yellow | " | " |
| 1 | 0.5 | 18 | 45 | No | pale yellow | " | No |
| 2 | 0.4 | 27 | 50 | " | " | " | " |
| 3 | 0.8 | 35 | 46 | " | " | " | " |
| 4 | 1.8 | 100 or more | 120 | " | " | " | " |
| 5 | 1.7 | 34 | 90 | " | " | " | " |
| 6 | 3.1 | 75 | 155 | " | " | " | " |
| 7 | 2.0 | 7 | 42 | " | " | " | " |
| 8 | 2.5 | 2 | 30 | " | " | " | " |
| 9 | 1.2 | 35 | 71 | " | " | " | " |
| 10 | 1.5 | 100 or more | 105 | " | " | " | " |
| 11 | 3.1 | 20 | 42 | " | " | " | " |
| 12 | 4.4 | 52 | 36 | " | " | " | " |
| 13 | 4.1 | 18 | 54 | " | " | " | " |
| 14 | 5.1 | 38 | 47 | " | " | " | " |
| 15 | 3.3 | 25 | 41 | " | " | " | " |
| 16 | 4.2 | 75 | 65 | " | " | " | " |

*This is defined as the maximum concentration (%) at which the ester can be clearly dissolved in an ethanol/water (50/50) solution.
**This was evaluated by applying the sample to a piece of celluloid, allowing it to stand at 70° C. for 1 hour, and then observing its surface conditions.

EXAMPLE 17

A liquid hairdressing was prepared by adding 20 parts of the esterification product of Example 5 and 0.5 part of a perfume to 79.5 parts of ethanol/water (50/50) solution and stirring the mixture at 40° C. until a homogeneous solution was formed. The hairdressing thus obtained had an excellent hairdressing effect and permitted any hairdo to be achieved softly. Moreover, the hair could be shampooed easily and no attack on celluloid products was noted.

EXAMPLE 18

A water-soluble pasty hairdressing was prepared by mixing 60 parts of the ester of Example 10 with 25 parts of polypropylene glycol having an average molecular weight of about 2,000 and 14 parts of polypropylene glycol having an average molecular weight of about 700. To this mixture, one part of a perfume and an adequate amount of an antioxidant were added with stirring.

EXAMPLE 19

An astringent lotion was prepared by dissolving 0.8 part of alum, 4.0 parts of glycerol, and 6.0 parts of the ester of Example 6 in 77.8 parts of purified water. To this solution, a solution of 0.2 part of a perfume and 1.0 part of polyoxyethylene oleyl alcohol ether in 10.0 parts of ethanol was added and mixed well.

EXAMPLE 20

A liquid hairdressing was prepared by adding 20 parts of the ester of Example 14 and 0.5 part of a perfume to 79.5 parts of ethanol/water (50/50) solution and stirring the mixture at 40° C. until a homogeneous solution was formed.

What we claim is:

1. A polymeric ester obtained by reacting (A) at least one polymeric glycol represented by the general formula

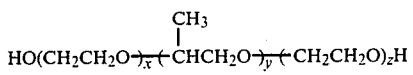

where the sum of x and y has an average value of from 1 to 50, y has an average value of from 10 to 60, and the total content of ethylene glycol units in all molecules is from 5 to 50% by weight, with (B) at least one carboxylic acid selected from the group consisting of saturated aliphatic dicarboxylic acids and saturated aliphatic hydroxydicarboxylic acids.

2. A polymeric ester as claimed in claim 1 wherein the sum of x and y has an average value of 3 to 20.

3. A polymeric ester as claimed in claim 2 wherein y has an average value of 15 to 40.

4. A polymeric ester as claimed in claim 3 wherein the total content of ethylene glycol units is 10 to 30% by weight.

5. A polymeric ester as claimed in claim 1 wherein said carboxylic acid is represented by the general formula

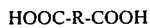

where R is an alkylene group having from 2 to 8 carbon atoms.

6. A polymeric ester as claimed in claim 5 wherein said carboxylic acid is succinic acid.

7. A polymeric ester as claimed in claim 1 wherein said carboxylic acid is malic acid or tartaric acid.

* * * * *